(12) United States Patent
Sharkey et al.

(10) Patent No.: US 8,574,303 B2
(45) Date of Patent: *Nov. 5, 2013

(54) OSTEOARTHRITIS TREATMENT AND DEVICE

(75) Inventors: Peter F. Sharkey, Villanova, PA (US); Charles F. Leinberry, Chester Springs, PA (US)

(73) Assignee: Zimmer GmbH, Inc. (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/273,912

(22) Filed: Oct. 14, 2011

(65) Prior Publication Data

US 2012/0035673 A1    Feb. 9, 2012

Related U.S. Application Data

(63) Continuation of application No. 12/110,434, filed on Apr. 28, 2008, now Pat. No. 8,062,364.

(60) Provisional application No. 60/914,465, filed on Apr. 27, 2007.

(51) Int. Cl.
    *A61F 2/38*    (2006.01)

(52) U.S. Cl.
    USPC .................. 623/20.14; 623/23.58; 623/908

(58) Field of Classification Search
    None
    See application file for complete search history.

(56) References Cited

U.S. PATENT DOCUMENTS

| 5,273,964 | A |   | 12/1993 | Lemons |
|---|---|---|---|---|
| 5,514,137 | A |   | 5/1996 | Coutts |
| 5,556,429 | A | * | 9/1996 | Felt ............................... 128/898 |
| 5,755,809 | A |   | 5/1998 | Cohen et al. |
| 5,902,825 | A |   | 5/1999 | Jia |
| 6,140,452 | A |   | 10/2000 | Felt et al. |
| 6,235,043 | B1 |   | 5/2001 | Reiley et al. |

(Continued)

FOREIGN PATENT DOCUMENTS

| RU | 2161929 |   | 1/2001 |
|---|---|---|---|
| RU | 2161929 C1 | * | 1/2001 |
| WO | 2004080384 |   | 9/2004 |
| WO | WO 2005107614 A1 | * | 11/2005 |

OTHER PUBLICATIONS

Wluka, et al.; "The Clinical Correlates of Articular Cartilage Defects in Symptomatic Knee Osteoarthritis: A Prospective Study"; Rheumatology, Jul. 2005, 44:1311-1316.*

(Continued)

*Primary Examiner* — David H Willse
*Assistant Examiner* — Javier Blanco
(74) *Attorney, Agent, or Firm* — Monument IP Law Group

(57) ABSTRACT

A method for treating arthritis of a joint includes identifying a bone lesion in a bone adjacent to the joint; and implanting in the bone a reinforcing member in or adjacent to the bone lesion. A kit for conducting the method includes: (a) at least one reinforcing member having a proximal face adapted to face the joint, a distal face adapted to face away from the joint, and a wedge-shaped edge adapted to pierce bone, wherein the at least one reinforcing member is planar and sterile; and (b) a container adapted to maintain the at least one reinforcing member sterile. Another kit includes: (a) a sterile fluid; (b) a syringe for injecting the fluid into a bone; (c) a curing agent adapted to cure the fluid to polymerize and/or cross-link; and (d) a container adapted to maintain the sterility of contents of the container.

29 Claims, 1 Drawing Sheet

(56) References Cited

U.S. PATENT DOCUMENTS

| | | | |
|---|---|---|---|
| 6,241,734 | B1 | 6/2001 | Scribner et al. |
| 6,248,110 | B1 | 6/2001 | Reiley et al. |
| 6,280,474 | B1 | 8/2001 | Cassidy et al. |
| 6,306,177 | B1 | 10/2001 | Felt et al. |
| 6,395,007 | B1 | 5/2002 | Bhatnagar et al. |
| 6,527,810 | B2 | 3/2003 | Johnson et al. |
| 6,564,083 | B2 * | 5/2003 | Stevens .................. 600/410 |
| 6,607,561 | B2 | 8/2003 | Brannon |
| 6,613,054 | B2 | 9/2003 | Scribner et al. |
| 6,711,432 | B1 * | 3/2004 | Krause et al. ............ 600/427 |
| 6,719,761 | B1 | 4/2004 | Reiley et al. |
| 6,746,451 | B2 | 6/2004 | Middleton et al. |
| 6,767,369 | B2 | 7/2004 | Boyer, II et al. |
| 6,818,018 | B1 | 11/2004 | Sawhney |
| 6,827,720 | B2 | 12/2004 | Leali |
| 6,863,899 | B2 | 3/2005 | Koblish et al. |
| 6,887,246 | B2 | 5/2005 | Bhatnagar et al. |
| 7,153,307 | B2 | 12/2006 | Scribner et al. |
| 7,166,570 | B2 | 1/2007 | Hunter et al. |
| 7,261,720 | B2 | 8/2007 | Stevens et al. |
| 7,425,549 | B2 | 9/2008 | Little et al. |
| 7,442,195 | B1 | 10/2008 | Behrens |
| 7,708,742 | B2 | 5/2010 | Scribner et al. |
| 7,771,431 | B2 | 8/2010 | Scribner et al. |
| 7,811,290 | B2 | 10/2010 | Rabiner |
| 8,152,813 | B2 | 4/2012 | Osorio et al. |
| 8,168,692 | B2 | 5/2012 | Wenz |
| 2003/0055316 | A1 | 3/2003 | Brannon |
| 2003/0055431 | A1 | 3/2003 | Brannon |
| 2003/0135214 | A1 | 7/2003 | Fetto et al. |
| 2003/0138473 | A1 | 7/2003 | Koblish et al. |
| 2005/0101673 | A1 | 5/2005 | Norden et al. |
| 2005/0119219 | A1 * | 6/2005 | Bellini et al. ............. 514/54 |
| 2005/0177169 | A1 * | 8/2005 | Fisher et al. ............. 606/88 |
| 2005/0251266 | A1 | 11/2005 | Maspero et al. |
| 2006/0057184 | A1 | 3/2006 | Nycz et al. |
| 2006/0064164 | A1 | 3/2006 | Thelen et al. |
| 2006/0172934 | A1 | 8/2006 | Nycz et al. |
| 2007/0010440 | A1 | 1/2007 | Schense et al. |
| 2007/0123894 | A1 | 5/2007 | Claypool et al. |
| 2007/0259018 | A1 | 11/2007 | McKay |
| 2007/0275028 | A1 | 11/2007 | Barry et al. |
| 2007/0287988 | A1 | 12/2007 | Trebing et al. |
| 2008/0031915 | A1 | 2/2008 | Becerra Ratia et al. |
| 2008/0113008 | A1 | 5/2008 | Roche |
| 2008/0294085 | A1 | 11/2008 | Stamps et al. |
| 2008/0294269 | A1 | 11/2008 | Fell |
| 2009/0081169 | A1 | 3/2009 | Egrise et al. |
| 2009/0123378 | A1 | 5/2009 | Wong et al. |
| 2010/0076503 | A1 | 3/2010 | Beyar et al. |
| 2010/0145451 | A1 | 6/2010 | Dee |
| 2010/0179549 | A1 | 7/2010 | Keller et al. |

OTHER PUBLICATIONS

Altman, et al., "Development of Criteria for the Classification and Reporting of Osteoarthritis, Classification of Osteoarthritis in the Knee: Classification of Osteoarthritis of the Knee", Arthritis & Rheumatism, Aug. 1986, 29(8): 1039-1049.

Baranyay, et al., "Association of Bone Marrow Lesions with Knee Structures and Risk Factors for Bone Marrow Lesions in the Knees of Clinically Healthy, Community-Based Adults", Seminar in Arthritis & Rheumatism, Oct. 2007: 112-118.

Bingham, et al., "Risedronate Decreases Biochemical Markers of Cartilage Degradation but Does Not Decrease Symptoms of Slow Radiographic Progression in Patients with Medial Compartment Osteoarthritis of the Knee: Results of the Two-Year Mulitnational Knee Osteoarthritis Structural Arthritis Study", Arthritis & Rheumatism, Nov. 2006, 54(11): 3494-3507.

Buckland-Wright, et al., "A 2 Yr Longitudinal Radiographic Study Examining the Effect of a Bisphosphonate (Risedronate) Upon Subchondral bone Loss in Osteoarthritic Knee Patients", Rheumatology 2006, 46: 257-264.

Carbone, et al., "The Relationship of Antiresorptive Drug Use to Structural Findings and Symptoms of Knee Osteoarthritis", Arthritis & Rheumatism, Nov. 2004, 50(11): 3516-3525.

Cicuttini, et al., "Association of Cartilage Defects with Loss of Knee Cartilage in Healthy, Middle-Aged Adults: A Prospective Study", Arthritis & Rheumatism, Jul. 2005, 57(7): 2033-2039.

Cicuttini, et al., Comparison of Tibial Cartilage Volume and Radiologic Grade of the Tibiofemoral Joint:, Arthritis & Rheumatism, Mar. 2003, 48(3): 682-688.

Glegg, et al., "Glucosamine, Chondroitin Sulfate, and the Two in Combination for Painful Knee Osteoarthritis", The New England Journal of Medicine, Feb. 2006, 354(8): 795-808.

Felson, et al., "Correlation of the Development of Knee Pain With Enlarging Bone Marrow Lesions of Magnetic Resonance Imaging", Arthritis & Rheumatism, Sep. 2007, 58(9): 2986-2992.

Felson, et al., "An Update on the Epidemiology of Knee and Hip Osteoarthiritis with a View to Prevention", Athritis & Rheumatism, Aug. 1998, 41(8): 1343-1355.

Felson, et al., "Obesity and Knee Osteoarthritis, the Framingham Study", Annals of Internal Medicine, Jul. 1988, 109: 18-24.

Felson, et al., "Osteoarthritis: Is it a Disease of Cartilage or of Bone?", Arthritis & Rheumatism, Feb. 2004, 50 (2): 341-344.

Felson, et al., "The Prevalence of Knee Osteoarthritis in the Elderly, The Framingham Osteoarthritis Study", Arthritis & Rheumatism, Aug. 1987, 30(8): 914-918.

Garnero, et al., "Bone Marrow Abnormalities on Magnetic Resonance Imaging Are Associated with Type II Collagen Degradation in Knee Osteoarthritis: A Three-Month Longitudinal Study", Arthritis & Rheumatism, Sep. 2005, 52 (9): 2822-2829.

Guymer, et al., "A Study of the Prevalence and Association of Subchondral Bone Marrow Lesions in the Knees of Healthy, Middle-Aged Women", Osteoarthritis and Cartilage, Dec. 2007, 15(12): 1437-1442.

Hunter, et al., "Bone marrow lesions from osteoarthritis knees are characterized by sclerotic bone that is less well mineralized", Arthritis Research & Therapy; Jan. 2009, 11(1): http://arthritis-research.com/content/11/R11.

Hunter, et al., "Increase in Bone Marrow Lesions Associated with Cartilage Loss: A Longitudinal Magnetic Resonance Imaging Study of Knee Osteoarthritis", Arthritis & Rheumatism, May 2006, 54(5): 1529-1535.

Jones, et al., "Early Radiographic Osteoarthritis is Associated with Substantial Changes in Cartilage Volume and Tibial Bone Surface Area in Both Males and Females", Osteoarthritis and Cartilage, Feb. 2004, 12(2): 169-174.

Mayerhoefer, et al., "Short-term outcome of painful bone marrow oedema of the knee following oral treatment with iloprost of tramadol: results of an exporatory phase II study of 41 patients", Rheumatology 2007, Jul. 2007: 1-6.

McQueen, F.M., "A vital clue to deciphering bone pathology: MRI bone oedema in rheumatoid arthritis and osteoarthritis", Annals of Rheumatic Diseases 2007, 66: 1549-1552.

Radin, et al., "Role of Subchondral Bone in the Initiation and Progression of Cartilage Damage", Clinical Orthopaedics and Related Research, Dec. 1986, 213: 34-40.

Segal, et al., "Baseline Articular Contact Stress Levels Predict Incident Symptomatic Knee Osteoarthritis Development in the MOST Cohort", Journal of Orthopaedic Research, Dec. 2009: 1562-1568.

Wang, et al., "Factors Affecting Progression of Knee Cartilage Defects in Normal Subjects Over 2 Years", Rheumatology, Sep. 2006, 45: 79-84.

Wilson, et al., "Expression of Glutamate Receptors and Transporters in Human Subchondral Bone in Osteoarthritis", Paper #23, Knee Society Meeting in Boston, MA (Oct. 2009).

Wluka, et al., Bone Marrow Lesions Predict Progression of Cartilage Defects and Loss of Cartilage Volume in Healthy Middle-Aged Adults Without Knee Pair Over 2 Years, Rheumatology, Jul. 2008.

(56) References Cited

OTHER PUBLICATIONS

Wluka, et al., "The Clinical Correlates of Articular Cartilage Defects in Symptomatic Knee Osteoarthritis: A Prospective Study", Rheumatology, Jul. 2005, 44: 1311-1316.

Arnoldi, et al., "Intraosseous Phlebography, Intraosseous Pressure Measurements and 99mTC-Polyphosphate Scintigraphy in Patients with Various Painful Conditions in the Hip and Knee", Acta Orthrop Scand. 1980;51: 19-28.

Bollet, "Edema of the bone marrow can cause pain in osteoarthritis and other diseases of bone and joints", Ann Intern Med., Apr. 3, 2001 134(7): 591-3.

Felson, et al., "The association of bone marrow lesions with pain in knee osteoarthritis", Ann Intern Med., Apr. 3, 2001; 134(7): 541-9.

Felson, et al., "Bone marrow edema and its relation to progression of knee osteoarthritis", Ann Intern Med., Sep. 2, 2003; 139(5 Pt 1): 330-6.

McAlindon, et al., "Magnetic resonance imaging in osteoarthritis of the knee: correlation with radiographic and scintigraphic findings", Ann Rheum Dis., 1991; 50: 14-9.

Zanetti, et al., "Bone Marrow Edema Pattern in Osteoarthritic Knees: Correlation between MR Imaging and Histologic Findings", Radiology, 2000; 215: 835-840.

* cited by examiner

OSTEOARTHRITIS TREATMENT AND DEVICE

CROSS-REFERENCE TO RELATED APPLICATIONS

This is a continuation application of U.S. patent application Ser. No. 12/110,434 filed on Apr. 28, 2008, now U.S. Pat. No. 8,062,364, and entitled "OSTEOARTHRITIS TREATMENT AND DEVICE," which claims priority to U.S. Provisional Application No. 60/914,465 filed on Apr. 27, 2007, and entitled "OSTEOARTHRITIS TREATMENT AND DEVICE," the contents of which are herein incorporated by reference in their entirety.

FIELD

This invention relates to a method and device for treating osteoarthritis, particularly osteoarthritis of the knee.

BACKGROUND

Osteoarthritis is the most common form of arthritis, affecting the hands, knees, hips, spine and other joints. Characteristics of osteoarthritis include a loss of cartilage, seen as a reduction in the joint space, and osteophytes (or bone spurs).

Arthritic pain is a leading cause of lost productivity. The cause of arthritic pain is unclear. The amount of cartilage loss correlates poorly with the severity of pain in an afflicted individual. Likewise, radiographic finding such as osteophytes (bone spurs) and thickening of subchondral bone (eburination) do not correlate with the presence or severity of pain.

Bone marrow lesions (or edemas) are very strongly associated with knee arthritis pain (Felson et al., "The association of bone marrow lesions with pain in knee osteoarthritis." Ann Intern Med. 2001 Apr. 3; 134(7):541-9) and disease progression (Felson et al., "Bone marrow edema and its relation to progression of knee osteoarthritis." Ann Intern Med. 2003 Sep. 2; 139(5 Pt 1):330-6). See also U.S. Pat. No. 6,564,083 to Stevens, which describes a method of identifying in a patient having joint pain the susceptibility of the patient to developing progressive osteoarthritis or loss of joint space, by determining the presence or absence of bone marrow edema about or of the joint. The determination is preferably made through the use of Magnetic Resonance Imaging (MRI).

The nature and cause of bone marrow lesions is poorly understood. Histologic examination of these lesions demonstrates abnormal bone with areas of fibrosis, osteonecrosis and extensive bone remodeling (Zanetti et al., "Bone Marrow Edema Pattern in Osteoarthritic Knees Correlation between MR Imaging and Histologic Findings." Radiology. 2000; 215:835-840). It has been suggested that they are related to inflammation (Bollet, "Edema of the bone marrow can cause pain in osteoarthritis and other diseases of bone and joints." Ann Intern Med. 2001 Apr. 3; 134(7):591-3), venous hypertension (Arnoldi et al., "Intraosseous phlebography, intraosseous pressure measurements and 99 mTc-polyphosphate scintigraphy in patients with various painful conditions in the hip and knee." Acta Orthrop Scand. 1980; 51:19-28), or impaired arterial blood flow (McAlindon et al., "Magnetic resonance imaging in osteoarthritis of the knee: correlation with radiographic and scintigraphic findings." Ann Rheum. Dis. 1991; 50:14-9. Others have suggested these lesions reflect increased bone stress and microfracture of the bone (see Felson et al. 2003, supra).

Knee arthritis affects millions of people and the pain associated with this disease can be disabling. Patients who initially present with painful knee arthritis are usually treated non-surgically. Non-surgical treatments are modestly effective at temporarily relieving pain, but not risk free. Pharmacologic intervention (i.e., non-steroidal anti-inflammatory drugs) has been reported to be associated with significant complications, such as gastric ulcers, strokes and heart attacks. Steroid or viscosupplement injection may lead to infection. Steroid injections may also have systemic effects such as increased blood sugar and hypertension. Generally speaking non-surgical interventions are most efficacious for early arthritic disease and do not prevent disease progression.

When patients fail non-surgical treatment, surgical intervention is often recommended. Arthroscopic surgery has been shown to have limited effectiveness and has a small role in the management of knee arthritis. More invasive surgical approaches such as high tibial osteotomy and partial or complete knee replacement predictably relieve pain. However, these major operations are also potentially associated with significant morbidity and occasional mortality. These risks along with the limited durability of implantable devices influence patient and physicians to defer surgery until the symptoms become unbearable.

Accordingly, it is desired to provide an effective, surgical treatment of osteoarthritis, and particularly knee arthritis pain. It is further desired that such surgical treatment be less invasive than high tibial osteotomy and partial or complete knee replacement.

All references cited herein are incorporated herein by reference in their entireties.

SUMMARY

Accordingly, a first aspect of the invention comprises a method for treating arthritis of a joint, said method comprising: identifying a bone lesion in a bone adjacent to the joint; and implanting in the bone a reinforcing member in or adjacent to the bone lesion. The reinforcing member as implanted is preferably free of artificial bones to the bone. The method preferably decreases pain associated with arthritis and/or slows the progression of arthritis.

A second aspect of the invention comprises a kit for treating arthritis of a joint, said kit comprising: (a) at least one reinforcing member comprising a proximal face adapted to face the joint, a distal face adapted to face away from the joint, and a wedge-shaped edge adapted pierce bone, wherein the at least one reinforcing member is planar and sterile; and (b) a container adapted to maintain the at least one reinforcing member sterile.

A third aspect of the invention comprises a kit for treating arthritis of a joint, said kit comprising: (a) a sterile fluid; (b) a syringe for injecting the fluid into a bone; (c) a curing agent adapted to cure the fluid to polymerize and/or cross-link; and (d) a container adapted to maintain the sterility of contents of the container.

A fourth aspect of the invention comprises a method for treating arthritis of a joint, said method comprising: (a) identifying a bone lesion in a bone adjacent to the joint; and (b) implanting in the bone a reinforcing member in or adjacent to the bone lesion, wherein the method stabilizes the bone in order to prevent further biomechanical breakdown of the bone and of adjacent meniscal tissues, and alleviates pain in the joint.

BRIEF DESCRIPTION OF THE DRAWINGS

The invention will be described in conjunction with the following drawings in which like reference numeral designate like elements and wherein.

DESCRIPTION OF THE EMBODIMENTS

The invention is based on our theory that bone marrow lesions detected by MRI represent overstressed bone. Bone is continuously fatigued and damaged by everyday activity. However, bone is a living tissue and bone repair occurs in concert. Certain pathological processes, such as loss of joint cartilage, can disturb the equilibrium between bone damage and bone repair. Cartilage protects underlying bone shielding it from stress. In addition, loss of cartilage leads to joint deformity further increasing bone stress. Overstressed bone sustains more damage than repair, which results in pain.

The invention enhances the strength of bone, shielding bone from excessive stress. Strengthening the bone in accordance with the invention shifts the damage/repair equilibrium toward repair. In addition, strengthening the bone reduces, reverses and/or prevents the deformation of overstressed bone, which should relieve pain and slow arthritic disease progression within the underlying bone and adjacent meniscal tissues (cartilage).

The invention provides an additional treatment option for patients suffering with arthritic pain, particularly in the knee. Those individuals who have exhausted non-surgical care, but are not symptomatic enough or not prepared for other reasons (emotional, financial, etc.) to undergo more major surgical interventions, are ideal for treatment using the present invention. The method of the invention should be considered minor or outpatient surgery. The risk of complications is expected to be significantly less than with major arthritic surgery, such as high tibial osteotomy and partial or total knee replacement. Preferred embodiments of the inventive treatment stabilize the defect in the subchondral (underlying) bone in order to prevent further biomechanical breakdown of the bone and of the adjacent meniscal tissues, and alleviate the corresponding pain in the joint.

Figure 1:
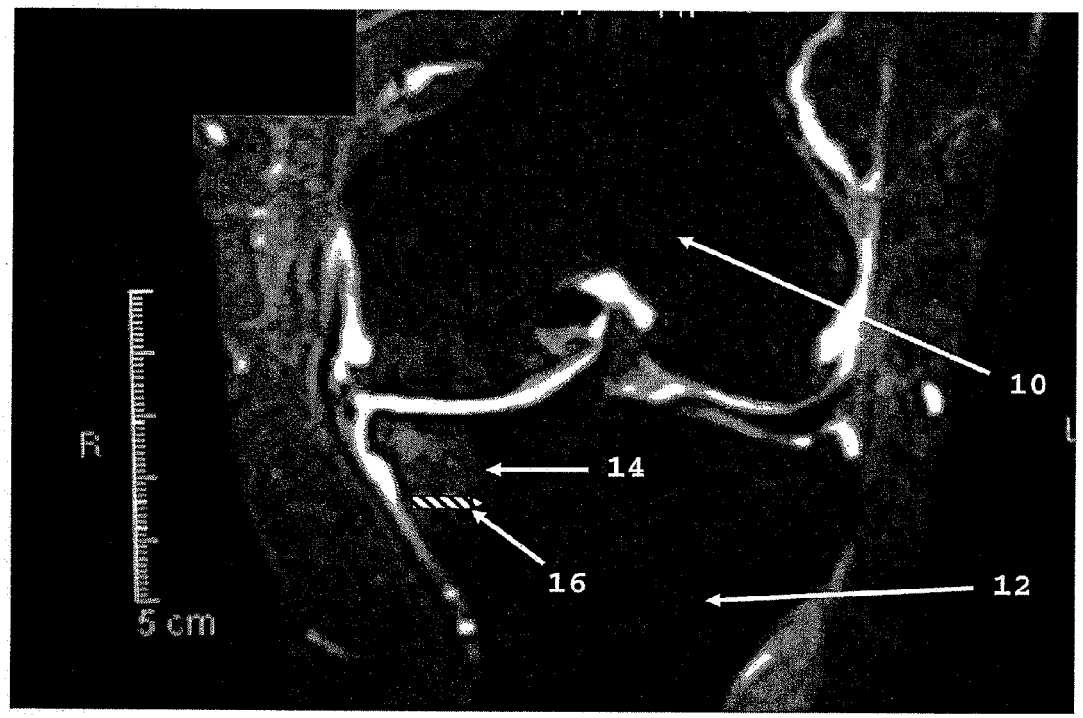
FIG. 1 is a magnetic resonance image (2D IR 1900/90/ 25.0; COR 200×180; 4.0 FFS; 256×144 pr.) of an arthritic knee on which is overlaid a side view of an embodiment of the reinforcing member of the invention.

The method of the invention comprises identifying a bone lesion in a bone adjacent to the joint, and implanting in the bone a reinforcing member in or adjacent to the bone lesion. Referring to FIG. 1, an arthritic human knee comprises femur 10 and tibia 12. Bone lesion 14 of tibia 12 presents as a focally increased signal in the marrow in an MRI of the knee. In certain embodiments, coronal spin-echo fat-saturated proton density and T2-weighted fat-saturated magnetic resonance images are preferred. Bone lesions thought to be associated with arthritis are less than 10 cm or 5 cm or 1 cm from the joint. Thus in preferred embodiments, the invention treats bone lesions which are from 0 to 10 cm from the joint, or 0 to 5 cm from the joint, or 0 to 1 cm from the joint.

The bone lesion is preferably identified using MRI, but in less preferred embodiments, other identification means may be employed. For example, bone lesions can be identified using Technetium-99 bone scans, because there is a close correlation between the presence of activity noted on Technetium-99 bone scans and bone marrow lesions. In embodiments of the invention employing MRI, any MRI technology that reveals bone marrow lesions can be used, for example, open MRI, low field strength MRI, extremity MRI, whole body scanner MRI or the like.

Reinforcing member 14 is preferably selected in accordance with the guidance provided by the following bone lesion grading system.

| Bone Lesion Grading System | | |
|---|---|---|
| Class | Bone Lesion Dimension | Comments |
| I | <1 mm | Bone healing is likely and resorbable graft materials are appropriate. Non-limiting exemplary materials for use as the reinforcing member include hyaluronic acid (HA), calcium phosphate (CaP) grafts, and cements (CaP & PMMA). |
| II | 1-3 mm | Bone healing is more challenging and a semi-structural graft material is appropriate. Non-limiting exemplary materials for use as the reinforcing mbmer include HA, CaP, cements (CaP & PMMA), and structural implants of metal and/or polymer. |
| III | 3-5 mm | Bone healing is less likely, and thus structural non-resorbing support is appropriate. Non-limiting exemplary materials for use as the reinforcing member include CaP cements, PMMA cements, and structural implants of metal and/or polymer. |
| IV | >5 mm | Bone healing is unlikely, and thus a permanent structural implant is required. Non-limiting exemplary materials for use as the reinforcing member include PMMA cements, and structural implants of metal and/or polymer. |

FIG. 1 shows a preferred example of how reinforcing member 16 could be implanted in bone lesion 14. It is also within the scope of the invention to implant the reinforcing member adjacent to the bone lesion. For example, the reinforcing member can be implanted adjacent to a side of the bone lesion proximal to the joint and/or adjacent to a side of the bone lesion distal to the joint. One or more than one reinforcing member can be implanted in and/or adjacent to a bone lesion. A reinforcing member is adjacent to a bone lesion if it is less than 10 cm away from an outer surface of the bone lesion. Adjacent reinforcing members can be in contact with an outer surface of the bone lesion. Thus in preferred embodiments, an adjacent reinforcing member can be from 0 to 10 cm from the bone lesions, or 0 to 5 cm from the bone lesion, or 0 to 1 cm from the bone lesion.

It is also preferred that the reinforcing member as implanted be free of bonds to the bone. Thus, the reinforcing member is preferably not, for example, glued, cemented, stapled, stitched, clamped or screwed to the bone. However, the expression "free of artificial bonds to the bone" does not exclude from such embodiments the possibility that bonds are formed by biological processes in situ.

The reinforcing member is implanted in the bone in or adjacent the bone lesion such that a proximal face faces the joint and a distal face faces away from the joint. Preferably, the reinforcing member is selected or modified (e.g., cut, torn, etc.) such that a maximum dimension of the proximal face exceeds a maximum dimension of the bone lesion. It is also within the scope of the invention for the maximum dimension of the bone lesion to equal or exceed a maximum dimension of the proximal face. Thus, the reinforcing member can be larger, smaller or the same size as the bone lesion. The reinforcing member is preferably implanted such that the proximal face is perpendicular to a longitudinal axis of the bone. It is preferred that the proximal and/or distal faces be the primary load bearing surfaces.

In certain embodiments, a syringe (optionally with a needle) can be used to inject a fluid into a bone so as to form the reinforcing member in situ. This step can be conducted with or without first creating an opening in the bone. The fluid is preferably a liquid, semi-solid, gel, hydrogel, dispersion or slurry. After injection, the fluid can remain in its originally-injected state, or can cure to a less fluid state. For example, the injected fluid can cross-link or polymerize from a liquid to form a semi-solid, gel or solid. Fluids that cure in situ can be self-curing or can cure in response to curing means, such as, e.g., radiation (e.g., UV light), heat (e.g., body temperature), moisture and/or a curing agent. See, e.g., U.S. Pat. Nos. 6,818,018 to Sawhney and 6,280,474 to Cassidy et al.

In certain embodiments, the reinforcing member is a solid or a non-fluid material that is not amenable to injection into the bone. In these embodiments, the surgeon creates a small opening in the vicinity of the bone lesion. Suitable surgical tools for this task include standard bone instruments (e.g., chisels, drills, etc.) and instruments specifically designed for use in the method of the invention. It is also possible to use the wedge-shaped edge of the reinforcing member to pierce the bone, preferably with assistance from a hammer.

Although it is within the scope of the invention for the surgeon to implant the reinforcing member by studying a previously captured image of the bone lesion and using his or her own senses to estimate the location and boundaries of the bone lesion, it is preferred that the surgeon be provided with additional guidance during surgery. For example, surgery can be conducted using real-time imaging, robotic devices, braces for maintaining the joint in a position consistent with captured images of the joint and/or labels. See, e.g., U.S. Pat. No. 6,711,432 to Krause et al. Suitable labels include but are not limited to radioactive labels, such as Technetium-99 and objects, such as fiducial markers.

Postoperatively, patients may be required to maintain partial weight bearing and use ambulatory aids. Depending upon the physician's discretion, full weight bearing may be possible. Routine post intervention physical therapy will likely be required. Additionally, patients will need routine post intervention care, observation and follow-up.

Figure 2:
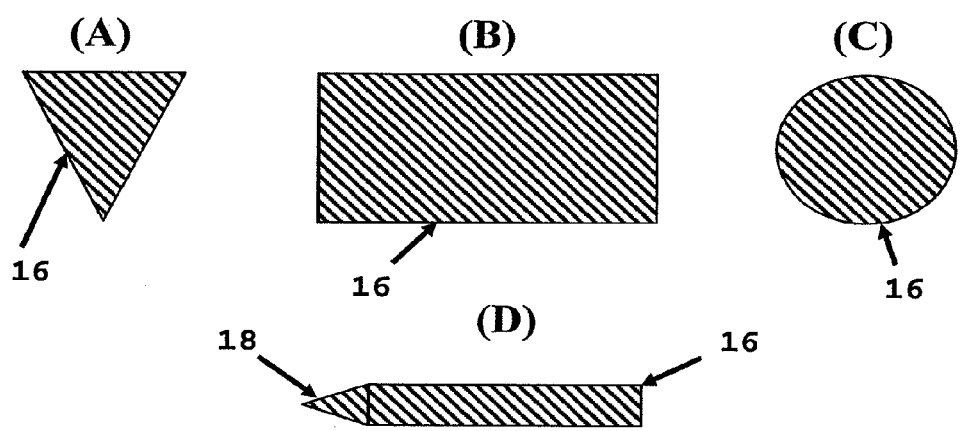
FIGS. 2A, 2B and 2C are overhead views of three embodiments of the reinforcing member of the invention.
FIG. 2D is a side view of the embodiment of FIG. 2B.

FIG. 2 shows several different embodiments of reinforcing members of the invention. FIG. 2A shows reinforcing member 16 having a triangular profile, FIG. 2B shows reinforcing member 16 having a rectangular profile and FIG. 2C shows reinforcing member 16 having a circular profile. Reinforcing member 16 is preferably planar, as seen from FIG. 2D, which shows a side view of the rectangular embodiment of FIG. 2C. The term "planar" as used herein refers to three-dimensional objects which are relatively long in two dimensions and relatively short in a third dimension. Planar reinforcing members in accordance with the invention can have a thickness which is ≤50% of the length and ≤50% of the width of a rectangular reinforcing member (or ≤50% of the diameter in the case of a circular reinforcing member or ≤50% of the height and ≤50% of the base in the case of a triangular reinforcing member).

As can be best seen in FIG. 2D, reinforcing member 16 has wedge-shaped edge 18 on at least one edge thereof. Wedge-shaped edge 18 is adapted to facilitate the step of driving reinforcing member 18 into the bone. Thus, the particular angle and other dimensions of the wedge are dictated by factors that are known in the art. Preferably, wedge-shaped edge 18 is similar to that found on standard surgical tools such as osteotomes or on implants such as blade plates or osteotomy staples.

Reinforcing member 16 comprises a physiologically compatible material that has sufficient durability to reinforce the overstressed bone of the bone lesion and bear physiologic loads. Preferred materials for the reinforcing member include metals, such as titanium, stainless steel, alloys of cobalt and chrome, tantalum, alloys of titanium and nickel and other superelastic metal alloys, such as taught by U.S. Pat. No. 6,527,810. Titanium "foam", tantalum, trabecular metals, nanoceramics or other hightly porous nanomaterials, and chrome cobalt are particularly preferred. Other embodiments comprise the use of bone, such as autografts, allografts, and artificial or synthetic bone substitutes. Certain embodiments comprise the use of polymeric materials.

Reinforcing member 16 is preferably osteogenic, osteoconductive and/or osteoinductive. The term "osteogenic" as used herein refers to the ability of the reinforcing member to promote the growth of new bone tissue. The term "osteoinductive" as used herein refers to the ability of the reinforcing member to recruit cells from the host that have the potential for forming new bone and repairing bone tissue. The term "osteoconductive" as used herein refers to the ability of a non-osteoinductive reinforcing member to serve as a substrate supporting bone growth. Osteoconductive materials that are suitable for use in the present invention are biologically acceptable and include but are not limited to collagen and the various forms of calcium phosphates including hydroxyapatite, tricalcium phosphate, and fluorapatite. Suitable osteoinductive substances include but are not limited to bone morphogenetic proteins (e.g., rhBMP-2), demineralized bone matrix, transforming growth factors (e.g., TGF-beta), osteoblast cells, and various other organic species known to induce bone formation. The osteoconductive and osteoinductive properties may be provided by bone marrow, blood plasma, or morselized bone of the patient, or commercially available materials. Osteoinductive materials such as BMP may be applied to articles of the invention, for example, by immersing the article in an aqueous solution of this material in a dilute suspension of type I collagen. Osteoinductive materials such as TGF-beta may be applied to an article of the invention from a saline solution containing an effective concentration of TGF-beta, or may be carried in the resilient material.

The reinforcing member can be resorbable, but is preferably non-resorbable, particularly when used to treat a chronic condition, such as osteoarthritis.

In certain embodiments, electrical stimulation is applied to the bone to promote bone healing.

The reinforcing member can be provided alone or in a kit according to the invention. A first embodiment of the kit includes at least one reinforcing member, which is sterile, and a container adapted to maintain the sterility of the at least one reinforcing member. Preferably, the containers are sealed flexible bags. The term "sterile" as used herein denotes a condition in which an object has a sterility assurance level (SAL) or $10^{-3}$ or less (preferably $10^{-6}$ of less) in accordance with current FDA guidelines for medical devices and as measured by AAMI/ISO 11607-1.

The first embodiment of the kit can optionally include an assortment of reinforcing members of various sizes and/or shapes appropriate for use with a variety of bone lesions. The kit can also include instructions for use, e.g., printed on the container and/or on inserts within the container. The kit can still further include a tool for adjusting the size of the reinforcing member, a hammer for driving the reinforcing member into the bone and/or a bone filler to seal the open end of the channel in the bone in which the reinforcing member resides. Suitable bone fillers include but are not limited to materials comprising beta-tricalcium phosphate (e.g., VITOSS, PROOSTEON 500R made by E-Interpore-Cross International), hydroxyapatite (e.g., OSTEOGRAF made by Ceramed Denta, Inc., Lakewood, Colo.), calcium carbonate, calcium sulfate (e.g., OSTEOSET and ALLOMATRIX made by Wright Medical Technology, Inc.), calcium phosphate (e.g., CALCIBON made by Merck & Co., Inc., Whitehouse Station, N.J. and NORIAN SRS made by Synthes-Strates, Switzerland), synthetic bone fillers (e.g., CORTOSS) and/or processed bone fillers (e.g., BIOOSS made by Geistlich Biomaterials, Inc., Switzerland). See U.S. Pat. No. 7,166,570.

A second embodiment of the kit includes a fluid, a syringe for injecting the fluid into a bone and a container adapted to maintain the sterility of the contents of the container. This embodiment of the kit can further comprise a needle and premeasured portions of ingredients in a plurality of separate vials. As with the first embodiment of the kit, this embodiment can optionally include instructions for use, e.g., printed on the container and/or on inserts within the container. The kit can further include bone tools for providing a channel in the bone in which the fluid is injected and/or a bone filler to seal the open end of the channel in the bone in which the reinforcing member resides. The kit can include curing agents (i.e., polymerizing agents, catalysts and/or crosslinking agents) as separate ingredients to be added to the injected fluid. The kit can include other curing means, such as a UV light source or other device for generating radiation. The fluid can be preloaded in the syringe for injection. In some embodiments, a multiple barrel syringe can be included for in situ mixing of ingredients that must be stored separately in different barrels of the syringe (e.g., monomers and polymerizing agent, or polymers and crosslinking agent, etc.).

While the invention is described in the context of osteoarthritis of the knee, it is not limited to such condition. Other conditions that can be treated in accordance with the invention include but are not limited to osteoarthritis of joints other than the knee.

While the invention has been described in detail and with reference to specific examples thereof, it will be apparent to one skilled in the art that various changes and modifications can be made therein without departing from the spirit and scope thereof.

What is claimed is:

1. A method of subchondrally treating pain associated with a subchondral defect of a knee joint with arthritis, the defect being attributed to overstressed bone as a result of a biomechanical breakdown of the bone or adjacent meniscal tissues, said method comprising:
   identifying a defect in a subchondral region of a bone of the joint based on capturing an image of said joint;
   determining, after identifying the defect, an extent of treatment based on size and shape of the defect;
   selecting at least one reinforcing member;
   creating, in said bone that contains the defect in its subchondral region, subchondral access into an area in or adjacent to the defect, while preserving an existing condition of the articular surface residing substantially over the subchondral region of said bone that contains the subchondral defect;
   implanting in the subchondral region of said bone the selected at least one reinforcing member in or adjacent to the subchondral defect via the subchondral access; and
   surgically stabilizing the defect in a manner that enhances the strength of the overstressed bone, the surgery being conducted with the use of guidance consistent with the image of said joint;
   wherein the stabilization alleviates corresponding pain in the joint.

2. The method of claim 1, further including the use of imaging labels.

3. The method of claim 2, wherein the imaging labels comprises radioactive labels.

4. The method of claim 1, further including the use of visual markers.

5. The method of claim 4, wherein the visual markers comprise fiducial markers.

6. The method of claim 1, wherein the step of identifying comprises magnetic resonance imaging.

7. The method of claim 1, wherein the step of identifying comprises a bone scan.

8. The method of claim 1, wherein the step of surgically stabilizing includes use of real-time imaging.

9. The method of claim 1, wherein the step of surgically stabilizing includes use of robotic devices.

10. The method of claim 1, wherein stabilizing the defect allows the overstressed bone to achieve more repair of bone tissue than damage under normal use.

11. The method of claim 1, wherein the step of surgically stabilizing includes use of mechanical braces.

12. The method of claim 1, wherein the defect comprises a bone marrow lesion.

13. The method of claim 1, wherein the overstressed bone comprises bone tissue that sustains more damage than repair under normal use.

14. The method of claim 1, wherein the at least one reinforcing member is selected in accordance with the size of the defect.

15. The method of claim 1, wherein stabilizing the defect reduces, reverses, or prevents deformation of the overstressed bone.

16. The method of claim 1, wherein stabilizing the defect slows the progression of arthritis.

17. The method of claim 1, wherein stabilizing the defect prevents further biomechanical breakdown of the bone or of adjacent meniscal tissues.

18. The method of claim 1, wherein the at least one reinforcing member is formed of a solid, a semi-solid or a gel material.

19. The method of claim 1, wherein the at least one reinforcing member is implanted by driving the member into the bone.

20. The method of claim 1, wherein the at least one reinforcing member is implanted within the defect.

21. The method of claim 1, wherein the at least one reinforcing member is formed in situ by injecting a fluid into the bone and curing the fluid.

22. The method of claim 1, wherein the at least one reinforcing member comprises a metallic, polymeric, autograft, allograft, artificial or synthetic bone substitute material.

23. The method of claim 1, wherein the at least one reinforcing member is osteogenic, osteoconductive or osteoinductive.

24. The method of claim 1, wherein the at least one reinforcing member is resorbable.

25. The method of claim 1, wherein preserving an existing condition of an articular surface of said bone comprises preserving an existing condition of a cartilage surface portion of said articular surface of said bone.

26. The method of claim 1, wherein the step of creating subchondral access comprises creating a channel in said bone.

27. The method of claim 26, wherein the step of creating a channel comprises use of tools for creating said channel in said bone.

28. The method of claim 1, wherein the at least one reinforcing member comprises a calcium phosphate.

29. A method of subchondrally treating pain associated with a subchondral defect of a knee joint with arthritis, the defect being attributed to overstressed bone as a result of a biomechanical breakdown of the bone or adjacent meniscal tissues, said method comprising:
- identifying a defect in a subchondral region of a bone of the joint based on capturing an image of said joint;
- determining, after identifying the defect, an extent of treatment based on size and shape of the defect;
- selecting at least one reinforcing member;
- creating, in said bone that contains the defect in its subchondral region, subchondral access into an area in or adjacent to the defect, while preserving an existing condition of the articular surface residing substantially over the subchondral region of said bone that contains the subchondral defect;
- implanting in the subchondral region of said bone the selected at least one reinforcing member in or adjacent to the subchondral defect via the subchondral access; and
- surgically stabilizing the defect in a manner that enhances the strength of the overstressed bone, the surgery being conducted with the use of real-time imaging of said joint;
- wherein the stabilization alleviates corresponding pain in the joint.

* * * * *